US010485647B2

(12) United States Patent
Gera et al.

(10) Patent No.: US 10,485,647 B2
(45) Date of Patent: Nov. 26, 2019

(54) INTRAVASCULAR DEVICE WITH MULTIPLE LEAFLETS

(71) Applicant: Keystone Heart Ltd., Caesarea (IL)

(72) Inventors: Moran Gera, Caesarea (IL); Yuval Shezifi, Haifa (IL)

(73) Assignee: Keystone Heart Ltd., Ceasarea (IL)

( * ) Notice: Subject to any disclaimer, the term of this patent is extended or adjusted under 35 U.S.C. 154(b) by 775 days.

(21) Appl. No.: 14/897,455

(22) PCT Filed: Jun. 11, 2014

(86) PCT No.: PCT/IL2014/050527
§ 371 (c)(1),
(2) Date: Dec. 10, 2015

(87) PCT Pub. No.: WO2014/199381
PCT Pub. Date: Dec. 18, 2014

(65) Prior Publication Data
US 2016/0120636 A1    May 5, 2016

Related U.S. Application Data

(60) Provisional application No. 61/834,164, filed on Jun. 12, 2013.

(51) Int. Cl.
*A61F 2/01*   (2006.01)

(52) U.S. Cl.
CPC ........ *A61F 2/013* (2013.01); *A61F 2002/016* (2013.01); *A61F 2210/0014* (2013.01); *A61F 2230/008* (2013.01)

(58) Field of Classification Search
CPC ................ A61F 2/013; A61F 2002/016; A61F 2210/0014; A61F 2230/008
See application file for complete search history.

(56) References Cited

U.S. PATENT DOCUMENTS

2012/0172915 A1*   7/2012   Fifer .................... A61F 2/013
                                              606/200

* cited by examiner

*Primary Examiner* — Ashley L Fishback
(74) *Attorney, Agent, or Firm* — Inskeep IP Group, Inc.

(57) ABSTRACT

This invention relates to devices that are inserted in a blood vessel or other body lumen, and in particular to filter that may block particles from entering a blood vessel. Devices of this invention position and secure a filter in a vascular system to intercept particulates, including emboli.

15 Claims, 15 Drawing Sheets

INTRAVASCULAR DEVICE WITH MULTIPLE LEAFLETS

CROSS-REFERENCE TO RELATED APPLICATIONS

This application claims benefit of U.S. Provisional Application No. 61/834,164 filed Jun. 12, 2013, which is hereby incorporated by reference in its entirety.

FIELD OF THE INVENTION

Embodiments of the invention relate to devices that are inserted in a blood vessel or other body lumen, and in particular to filter that may block particles from entering a blood vessel.

BACKGROUND OF THE INVENTION

Particles such as emboli may form, for example, as a result of the presence of particulate matter in the bloodstream. Particulate matter may originate from for example a blood clot occurring in the heart. The particulate may be a foreign body, but may also be derived from body tissues. For example, atherosclerosis, or hardening of the blood vessels from fatty and calcified deposits, may cause particulate emboli to form. Moreover, clots can form on the luminal surface of the atheroma, as platelets, fibrin, red blood cells and activated clotting factors may adhere to the surface of blood vessels to form a clot.

Blood clots or thrombi may also form in the veins of subjects who are immobilized, particularly in the legs of bedridden or other immobilized patients. These clots may then travel in the bloodstream, potentially to the arteries of the lungs, leading to a common, often-deadly disease called pulmonary embolus. Thrombus formation, and subsequent movement to form an embolus, may occur in the heart or other parts of the arterial system, causing acute reduction of blood supply and hence ischemia. The ischemic damage often leads to tissue necrosis of organs such as the kidneys, retina, bowel, heart, limbs, brain or other organs, or even death. Since emboli are typically particulate in nature, various types of filters have been proposed in an attempt to remove or divert such particles from the bloodstream before they can cause damage to bodily tissues.

SUMMARY OF THE INVENTION

In one aspect, the invention features an intravascular device to prevent a particle in the aorta from passing into a second blood vessel, the device containing: a primary frame containing: an elongated wire (e.g., a metal, metal alloy, shape memory material, plastic, polymer, silicone, ceramic, or a composite thereof, in which the material may be include a rigid, semi-rigid, or flexible material) having a first end and a second end, two or more supporting elements (e.g., two or more loops, chains, wires, fibers, or combinations thereof, in which the structure contains a metal, metal alloy, shape memory material, plastic, polymer, silicone, ceramic, or a composite thereof, in which the material may be include a rigid, semi-rigid, or flexible material), each of the supporting elements attached to the first end of the wire, and at least one expanding element (e.g., a flexible or semi-rigid material including one or more loops, twisted loops, circular elements, semi-circular elements, ovular elements, or a single flexible or semi-rigid loop) attached to the wire between the first end and the second end and configured to reversibly extend away from the wire; a filter (e.g., a plurality of woven fibers or a mesh in which the filter material includes a flexible metal, nitinol, a plastic, a polymer, a silicone, or a composite thereof having a pore size between about 50 microns (µm) to about 1000 µm, e.g., 50, 150, 250, 350, 450, 550, 650, 750, 850, 950, or more microns) containing: a distal end and a proximal end, and two or more leaflets, each of the leaflets containing a first attachment portion (e.g., a grommet), a second attachment portion, and a filter material having pores which are both large enough to allow blood to pass through and small enough to prevent a particle from passing through the filter; in which the supporting elements are attached to the first attachment portion of the leaflets and define the distal end of the filter, the second end of the wire may be attached to the second attachment portion of the leaflets (e.g., attached with an adhesive or weld) and define the proximal end of the filter, the two or more leaflets are configured to overlap with an adjacent leaflet to form a continuous filter surface, and the expanding element may be configured to contact and support the filter upon expansion; such that when the intravascular device may be deployed in an aortic arch, the elongated wire contacts a superior surface of the aortic arch, the distal end of the filter expands to fill the aorta and the proximal end of the filter converges to an apex, thereby preventing the bypass of fluid around the filter material and preventing a particle in the aorta from passing into a second blood vessel.

In some embodiments, the invention features a device in which the expanding element may be configured to apply a first force to the leaflets upon expansion thereby forming a continuous filter surface and continuous contact and/or a seal of the leaflets with surfaces of an aorta. In other embodiments, the invention features a device in which the supporting elements are configured to apply a second force to the leaflets, the second force maintaining a continuous filter surface and contacting the leaflets with an adjacent leaflet, thereby forming a seal between the leaflets. In some embodiments, the invention features an expanding element which may be reversibly extended by activation (e.g., twisting the wire) from the wire or a controllable catheter. In some embodiments, the invention features a filter which may be configured to be contracted during implantation and expanded upon deployment.

In some embodiments, at least a portion of one leaflet wraps around the wire of the primary frame. In any of the embodiments described herein, the invention may feature a device including at least two supporting elements, at least three supporting elements, at least four supporting elements, at least five supporting elements, or at least six supporting elements (e.g., 3, 4, 5, 6, 7, 8, 9, or 10 supporting elements). In some embodiments, the invention features a device including at least two expanding elements, at least three expanding elements, at least four expanding elements, at least five expanding elements, or at least six expanding elements. In any of the devices of the invention having leaflets, the device can include, e.g., three or more leaflets, four or more leaflets, five or more leaflets, or six or more leaflets (e.g., 3, 4, 5, 6, 7, 8, 9, or 10 leaflets).

In some embodiments, the invention features a device including a secondary frame containing a wire having a proximal end and a distal end, the distal end attached to the second end of the primary frame and the proximal end attached to a controllable catheter, the wire of the secondary frame having at least one stabilizing element (e.g., a flexible or semi-rigid material, one or more loops, twisted loops, circular elements, semi-circular elements, or ovular elements, or a single flexible or semi-rigid loop) attached to the wire between the distal and proximal ends and configured to simultaneously contact both superior and inferior surfaces of the aorta.

In some embodiments, the invention features a device in which the stabilizing element may be reversibly extended by activation (e.g., twisting the wire) from the wire or a controllable catheter. In some embodiments, the invention features a device in which the stabilizing element includes a metal, metal alloy, shape memory material (e.g., nitinol), plastic, polymer, silicone, ceramic, or a composite thereof.

In some embodiments, the invention features a device in which the elongated wire includes a tube (e.g., an aspirating tube). In some embodiments, tube includes an opening at the proximal end of the filter, configured to remove particles from the proximal end of the filter by applying a vacuum.

In one aspect, the invention features method of filtering particles in an aorta containing deploying the device of the invention in an aorta. In another aspect, the invention features a method of filtering particles in an aorta containing the following steps: a) collapsing one or more elements of a device of the invention, b) inserting the device into a catheter, c) inserting the catheter into an aortic arch, d) inserting the device into the aortic arch by removing the device from the catheter, e) expanding the one or more elements of the device, f) filtering blood flow, g) collapsing the one or more elements of the device, h) inserting the device into the catheter, and i) removing the catheter and the device. In some embodiments, the invention includes a device containing an aspirating tube and attached to vacuum source, and the particles are removed during step f) and before step h) by aspiration of the device.

In another aspect, the invention features an intravascular device to prevent a particle in the aorta from passing into a second blood vessel, the device containing: a primary frame containing: an elongated wire (e.g., a flexible or semi-rigid material, including a metal, metal alloy, shape memory material, plastic, polymer, silicone, ceramic, or a composite thereof) having a first end and a second end, at least one flexible expanding element having a proximal end, distal end, and an intervening portion, the distal end of the expanding element attached to the first end of the elongated wire, the proximal end of the expanding element attached to the second end of the elongated wire, and the intervening portion configured to reversibly extend away from the wire; a filter containing: a distal end and a proximal end, and two or more leaflets, each of the leaflets containing a first attachment portion, a second attachment portion, and a filter material (e.g., a plurality of woven fibers or a mesh in which the filter material includes a flexible metal, nitinol, a plastic, a polymer, a silicone, or a composite thereof having a pore size between about 50 microns (µm) to about 1000 µm, e.g., 50, 150, 250, 350, 450, 550, 650, 750, 850, 950, or more microns) having pores which are both large enough to allow blood to pass through and small enough to prevent a particle from passing through the filter; in which the intervening portion of the expanding element may be attached to the first attachment portion of the leaflets and may be adjacent to the distal end of the filter, the second end of the wire may be attached to the second attachment portion of the leaflets (e.g., with an adhesive or weld) and defines the proximal end of the filter; the two or more leaflets are configured to overlap with an adjacent leaflet to form a continuous filter surface; upon deployment, the distal end of the expanding element, reversibly moves towards the second end thereby reducing the distance there between, the expanding element may be configured to contact an surface of the aorta to support and form a seal between the filter and the aorta upon expansion such that, when the intravascular device may be deployed in an aortic arch, the distal end of the filter expands to fill the aorta and the proximal end of the filter converges to an apex, thereby preventing the bypass of fluid around the filter material and preventing a particle in the aorta from passing into a second blood vessel.

In some embodiments, the invention features a device in which the expanding element includes a planar structure extending beyond and substantially parallel to the first end and attached to the first end in a region of the expanding element adjacent to the planar structure and the planar structure may be attached to the first attachment portion of the leaflet. In other embodiments, the invention includes a device in which the expanding member may be expanded by moving the first end towards the second end, bending the planar structure away from the substantially parallel position and away from the elongated wire, thereby expanding the filter.

In another aspect, the invention features an intravascular device to prevent a particle from passing through a blood vessel, the device containing: a primary frame containing: an elongated wire (e.g., a flexible or semi-rigid material, including a metal, metal alloy, shape memory material, plastic, polymer, silicone, ceramic, or a composite thereof) having a first end and a second end, a cylindrical sheath, an activation tube having a proximal and distal end, and at least two expanding elements (e.g., curved elements) having a proximal end, distal end, and an intervening portion, the proximal end of the expanding element attached to the sheath, and the expanding element configured to reversibly extend away from the activation tube; a filter containing: a distal end and a proximal end, and two or more leaflets, each of the leaflets containing a first attachment portion (e.g., a grommet) located on the distal end of each of the two or more leaflets, a second attachment portion on the proximal end of each of the two or more leaflets, and a filter material (e.g., a plurality of woven fibers or a mesh in which the filter material includes a flexible metal, nitinol, a plastic, a polymer, a silicone, or a composite thereof having a pore size between about 50 microns (µm) to about 1000 µm, (e.g., 50, 150, 250, 350, 450, 550, 650, 750, 850, 950, or more microns) having pores which are both large enough to allow blood to pass through and small enough to prevent a particle from passing through the filter; in which the distal end of each of the expanding elements may be attached to the first attachment portion of a corresponding leaflet, the second attachment portion of each of the leaflets attaches to the distal end of the activation tube (e.g., with an adhesive or weld), the second end of the wire may be attached to the sheath, the two or more leaflets are configured to overlap with an adjacent leaflet to form a continuous filter surface, and the expanding element may be configured to reversibly fit inside the sheath and expand upon removal from the sheath; such that when the intravascular device may be deployed in a blood vessel, the distal end of the filter expands to circumferentially contact the inner surface of the blood vessel, thereby preventing a particle from passing through the blood vessel.

In some embodiments, the invention features a device including an introducer cartridge. In some embodiments, the invention features a device in which the expanding element may be configured to apply a first force to the leaflets upon expansion thereby forming a continuous filter surface and continuous contact and/or a seal of the leaflets with surfaces of a vessel. In some embodiments, the expanding element includes one or more loops, twisted loops, circular elements, semi-circular elements, ovular elements, or a single flexible or semi-rigid loop. In some embodiments, the expanding element may be reversibly extended by activation (e.g., twisting the wire) from the wire or a controllable catheter. In some embodiments, the invention features a device in which the filter may be configured to be contracted during implantation and expanded upon deployment.

In another aspect, the invention features an intravascular device to prevent a particle from passing through a blood vessel, the device containing: a primary frame containing: an elongated wire (e.g., a metal, metal alloy, shape memory material, plastic, polymer, silicone, ceramic, or a composite thereof) having a first end and a second end, two elongated members extending from the first end of the elongated wire, and a flexible tube containing a linear region, a branch region, and a loop region, the tube containing the elongated wire in the linear region and the elongated members in the loop region, the flexible tube capable of maintaining an internal pressure greater than the external pressure, and containing a substantially circular filter (e.g., a single continuous sheet or two or more leaflets, including a plurality of woven fibers, mesh, a flexible metal, plastic, polymer, silicone, composite thereof, or a nitinol mesh), the filter having pores which are both large enough to allow blood to pass through and small enough to prevent a particle from passing through the filter; in which the substantially circular filter may be a) disposed outside the tube within the inner space formed by the loop region of the tube; and b) attached to the outer surface of the tube in the loop region; such that when the intravascular device may be deployed in a blood vessel, the loop region of the tube expands in response to an application of internal pressure to contact the inner surface and substantially seal a blood vessel, thereby preventing a particle from passing through the blood vessel.

In some embodiments, the invention features a device in which the distal end of the filter may be configured to allow the reversible passage or a surgical instrument. In some embodiments, the invention features a device in which the filter material extends away from the flexible tube forming an apex at the distal end of the filter. In some embodiments, the invention features a device in which the elongated wire spans the diameter of the loop region and attaches to the loop region in more than one location. In some embodiments, the invention features a device in which the filter may be configured to be contracted during implantation and expanded upon deployment.

Definitions

By "about" is meant ±10% of any recited value.

As used herein, the term "blood" refers to all or any of the following: red cells (erythrocytes), white cells (leukocytes), platelets (thrombocytes), and plasma.

By "continuous filter surface" is meant a surface formed of filter material such that substantially all the fluid flow must pass through the filter material (e.g., the filter material operates without fluid bypass). For example, a series of filter sheets may be sealed to each other with heat bonding (e.g., melted together). The filter sheets may be sealed into a device and then exposed to a fluid flow. Alternatively, the filter sheets may be overlapping, such that the resistance to flow between overlapping sections is significantly greater than the resistant to flow through the filter material. In this way, substantially all the fluid flow will pass through the filter material.

By "expanding element" is meant an element of a device frame in which the geometry, size, shape, or dimensions may be reversibly altered to provide mechanical support and alter the dimensions of a flexible filter. An expanding element may also expand and apply a force to seal a flexible filter against a vascular wall, thus preventing fluid bypass of the filter.

By "filter material" is meant a porous structure incorporated into a filter layer, structure, or sheet.

By "leaflet" is meant a filter material portion shaped and sized to fit together with other leaflets or filter material portions to form a coherent, larger filter material area. For example, several filter sheets may be cut into e.g., a diamond or a triangle shape. These filter sheets may be attached to each other at a single attachment point. Leaflets, when expanded, may form various 3D structures including cones, hemispheres, or sheets.

By "particle" is meant any particulate, emboli, aggregate, colloid, plaque, substance, or clot that may cause harm (e.g., cause a stroke) when allowed to move through a vascular system.

By "stabilizing element" is meant an element of a device frame in which the geometry, size, shape, or dimensions may be reversibly altered to provide a mechanical interaction with a subject's anatomy to, e.g., reversibly fix the location of an intravascular device.

By "subject" is meant a human or non-human animal (e.g., a mammal).

By "supporting element" is meant an element of a device which provides a force to counter an expanding element to stabilize a filter leaflet or another functional device structure.

Other features and advantages of the invention will be apparent from the Detailed Description and the claims.

Figure 1:
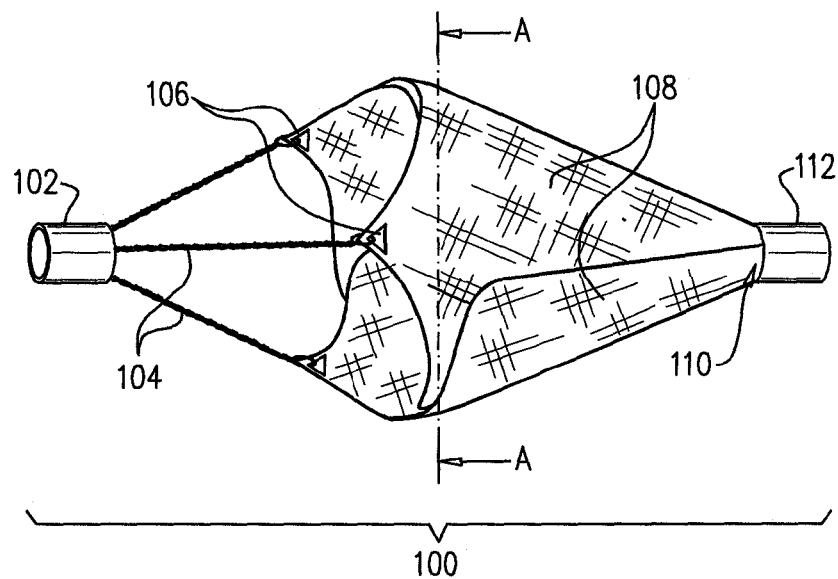
FIG. 1 is a schematic diagram of a side view of an exemplary intravascular device of the invention (100). The diagram shows three supporting elements (104), filter leaflets (108), and the first (106) and the second (110) attachment portions of the leaflets.

The diagram shows an intravascular device (300) installed in the aortic arch (202), with the filter leaflets (308) spanning the superior arteries of the aorta (e.g., the brachiocephalic artery (204), the left common artery (206), and the left subclavian artery (208)), beginning at the ascending aorta (200) and terminating at the descending aorta (210). The stabilizing element (318) contacts both the superior and inferior surfaces of the region where the aortic arch (202) meets the descending aorta (210), providing a stabilizing element for the intravascular device.

Figures 6A, 6B:
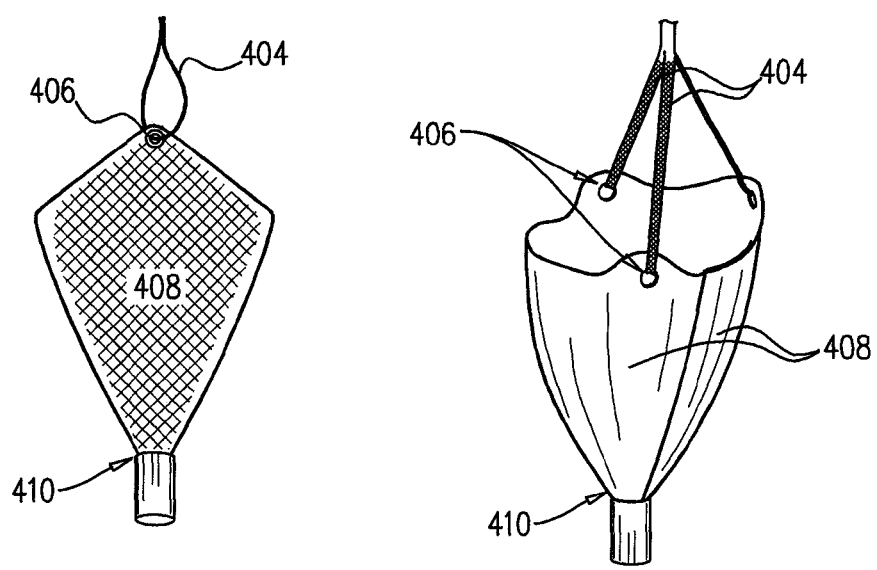

FIGS. 6A and 6B are schematic views of a single leaflet (408), first attachment portions (406), and second attachment portions (410), FIG. 6A, and the assembled intravascular device including multiple leaflets (408), first attachment portions (406), supporting elements (404), and second attachment portions (410), FIG. 6B.

Figure 7A:
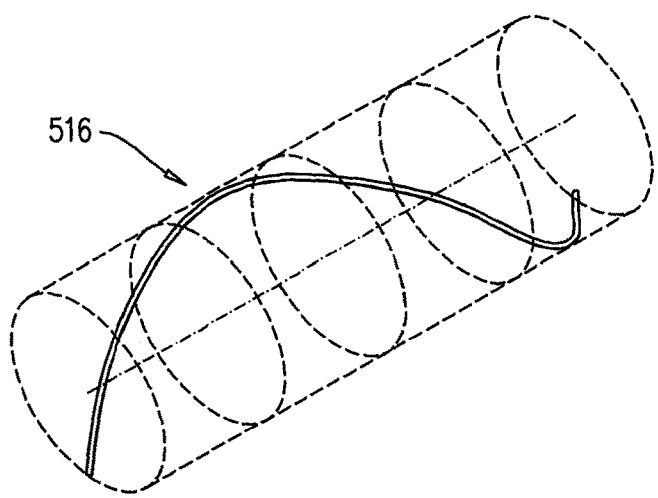
Figure 7B:
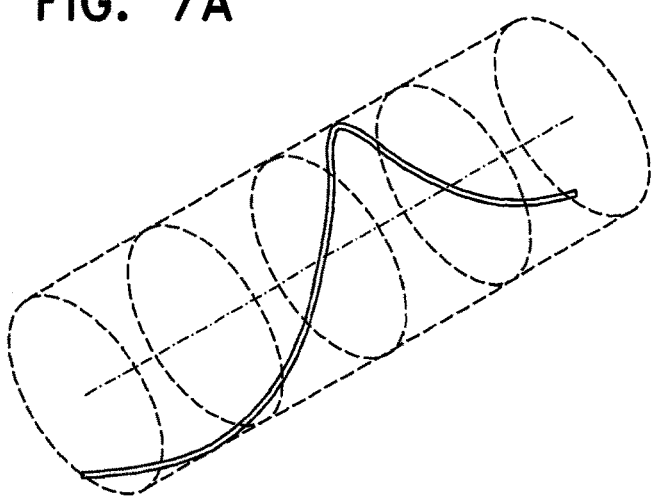
Figure 7C:
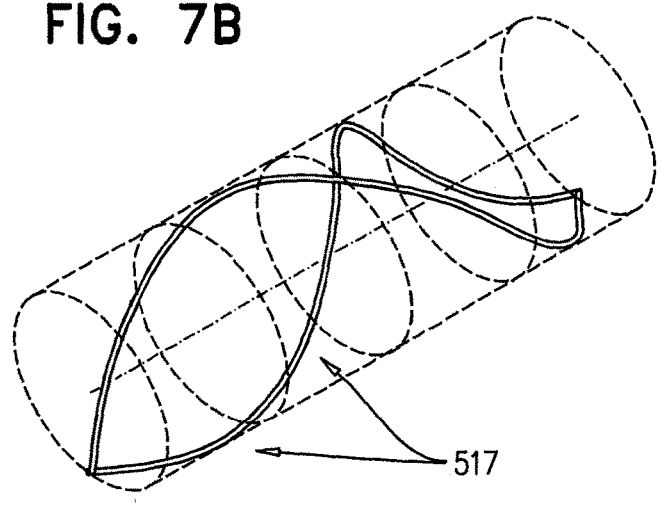

FIGS. 7A-7C are schematics of an exemplary expanding element of the invention (e.g., a loop). FIG. 7A is the expand element in an expanded state (516). FIG. 7B is the expanded element after a counter-clockwise turn. The loop begins to twist on to itself. FIG. 7C shows the expanding element in a collapsed state, in which the loop has collapsed on to itself (517).

Figure 8A:
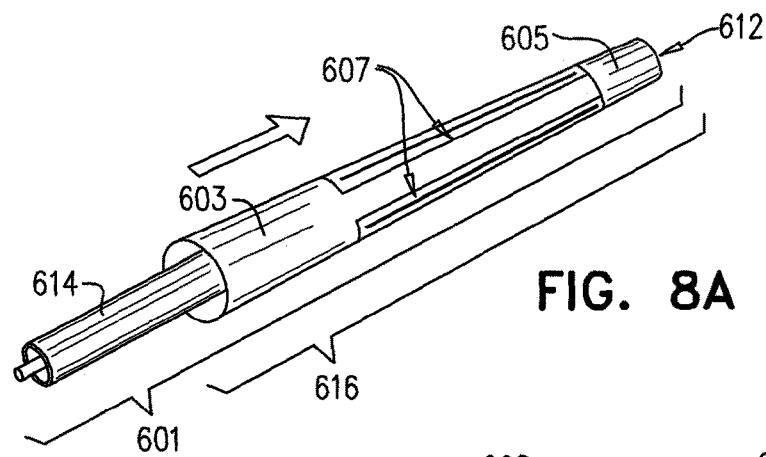
Figure 8B:
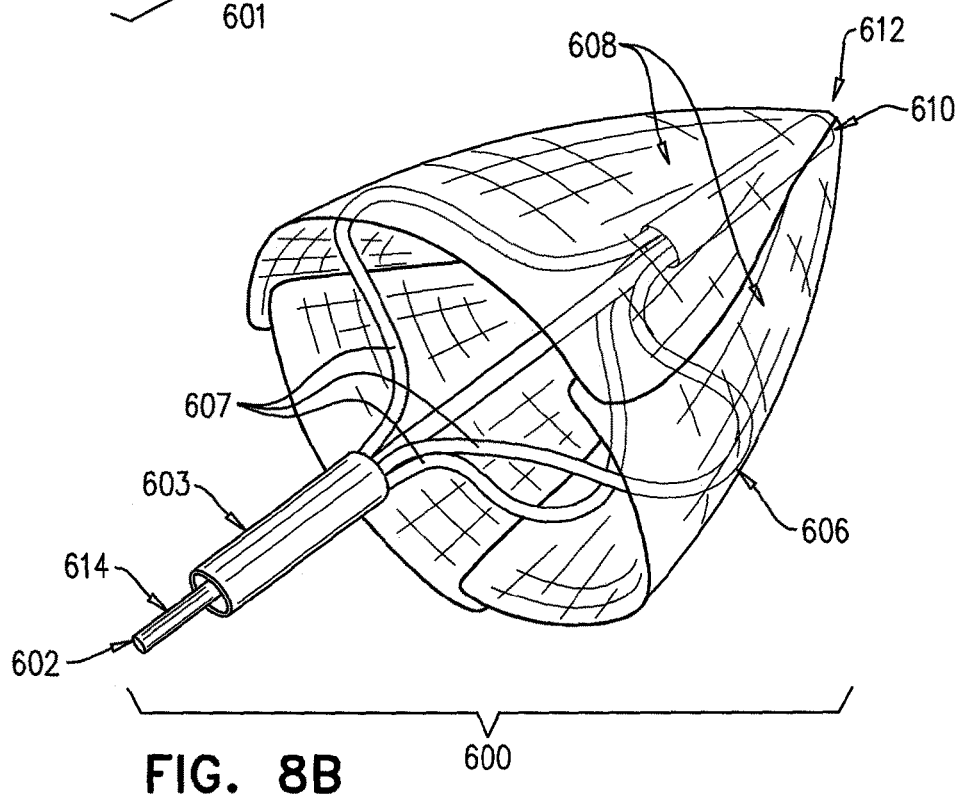
Figure 8C:
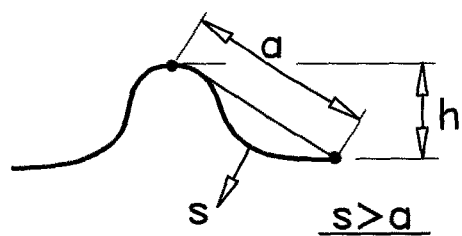

FIGS. 8A-8C are partially transparent schematics of an exemplary device of the invention, including expanding elements (616) attached to filter leaflets (608). FIG. 8A shows an elongated wire (614), first end (602), second end (612), and expanding elements (616) having a proximal end (605), distal end (603), and intervening portion (607) of the device in a collapsed (e.g., non-expanded state; filter leaflets not shown for clarity). FIG. 8B shows a device in an expanded state, including filter leaflets (608). The expanding elements attached to the first end (602) are expanded as the first end moves towards the second end (612). Filter leaflets attached to the expanding elements are expanded outward to form a cone like, continuous filter surface. FIG. 8C shows the relationship between the distance of the expanding element from the elongated wire (height, h), the length of the expanding element (length, S), and the distance moved by the first end towards the second end, as measured by the distance between the apex of the expanding element and the first end (distance, a). In this embodiment, the expanding elements operate as a combination of supporting and expanding elements because the intervening portion (607) of the expanding elements (616) are directly attached to the first attachment portion (606) of filter leaflets.

Figure 9A:
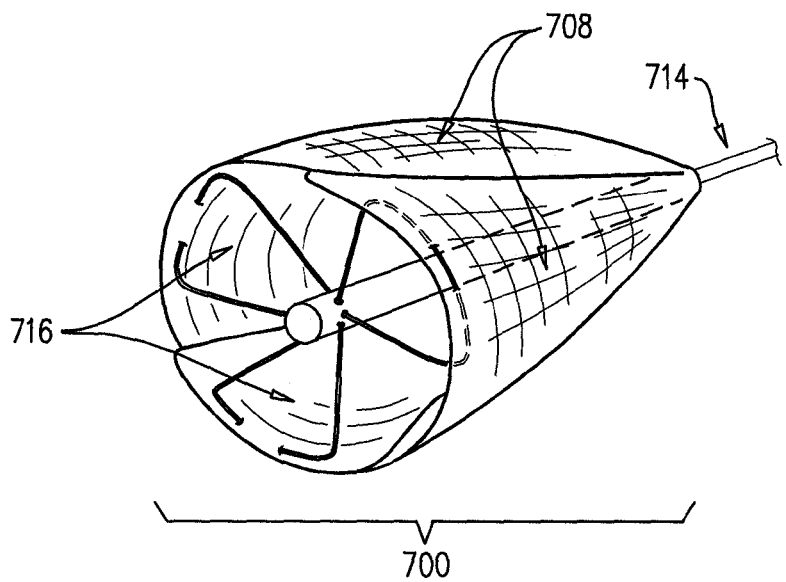
Figure 9B:
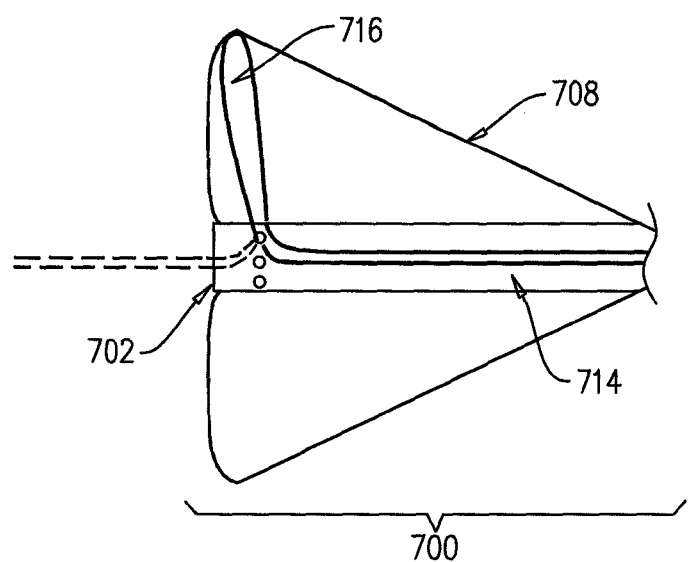

FIGS. 9A and 9B are partially transparent schematics of a device of the invention, including planar expanding elements (716) attached to filter leaflets (708). FIG. 9A shows a device (700) in an expanded state, with planar expanding elements (e.g., propeller or paddle shaped elements) attached to and expanding the filter leaflets to form a cone like, continuous filter. FIG. 9B is a schematic side view of the device, the dashed lines showing the position of the planar expanding element in a collapsed (e.g., non-expanded) state, and a solid line representation for the expanding element in a expanded state. In this embodiment, the expanding elements operate as a combination of supporting and expanding elements because the expanding elements are directly attached to the filter leaflets.

Figure 10A:
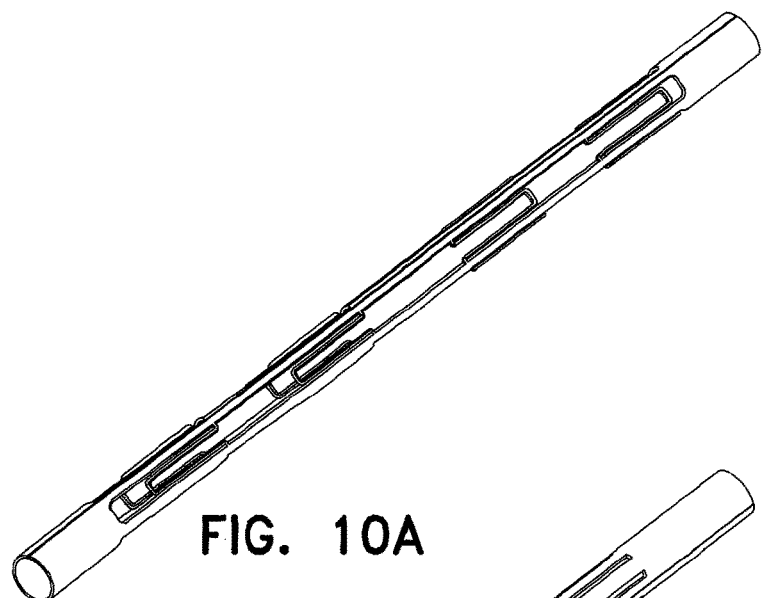
Figure 10B:
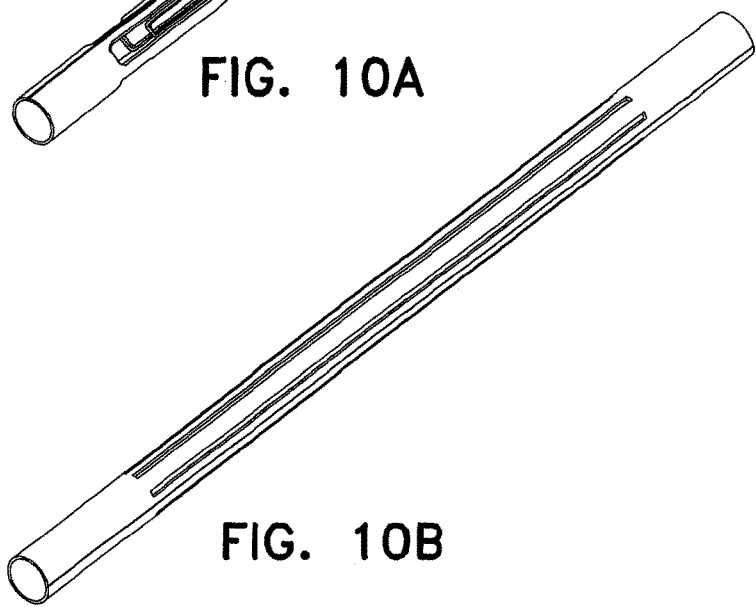
Figure 10C:
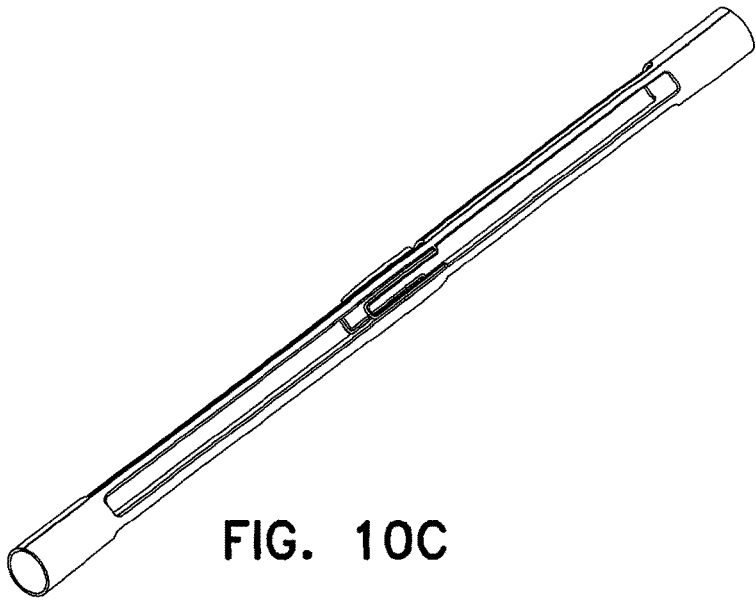

FIGS. 10A-10C are schematics of a device of the invention in a collapsed state (e.g., non-expanded state, filter leaflets not shown for clarity). FIG. 10A shows an elongated wire, a first end, a second end, and expanding elements collapsed and positioned for insertion into a catheter or elongated delivery tube. FIG. 10B and FIG. 10C are alternative component configurations including an elongated wire, a first end, a second end, and expanding elements.

Figure 11A:
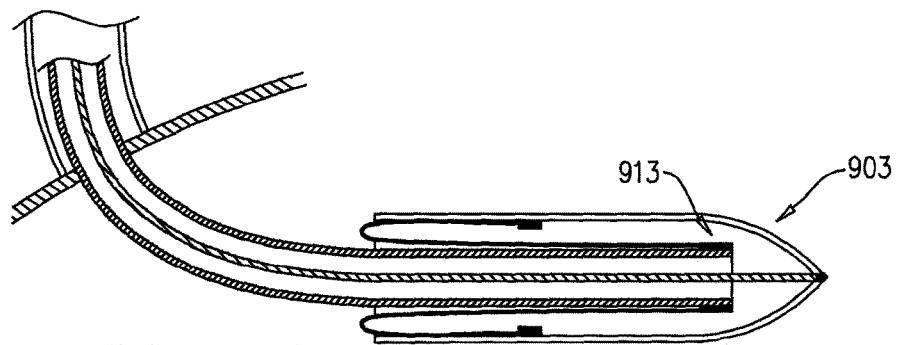
Figure 11B:
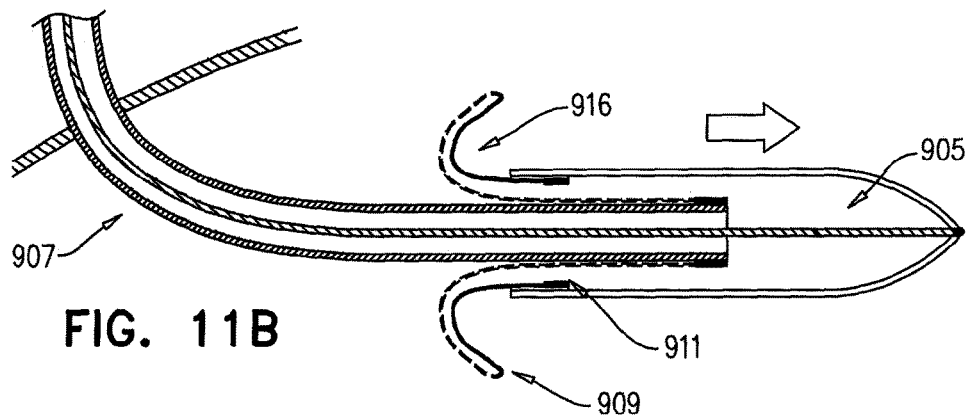
Figure 11C:
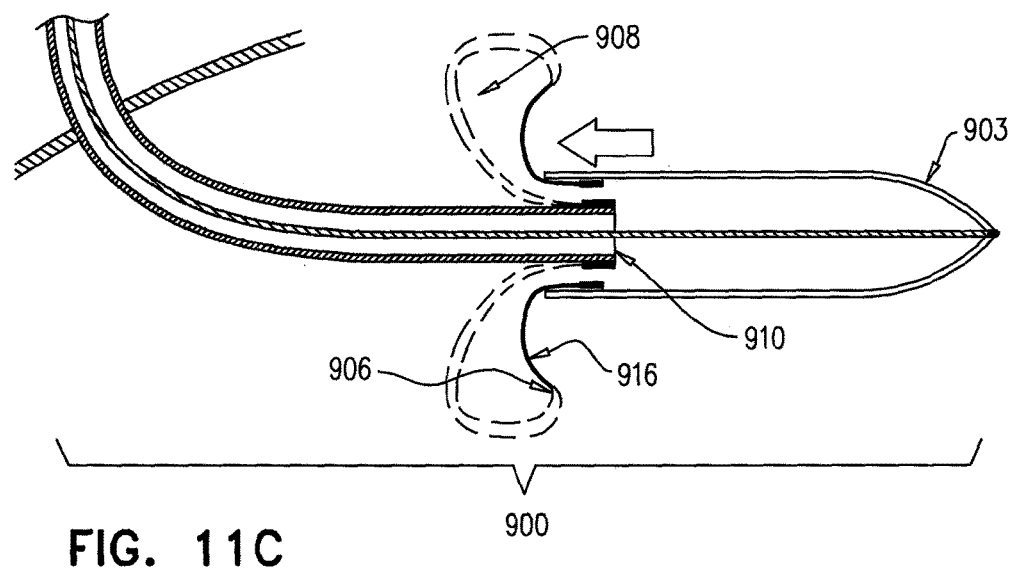

FIGS. 11A-11C are schematic cross-sectional views of an expanding device of the invention including a cylindrical sheath (903), activation tube (907), filter leaflets (908), elongated wire (905), and an expanding element (916). FIG. 11A shows the device in a non-expanded state (e.g., collapsed state for insertion into a delivery catheter of delivery device). FIG. 11B shows the device during installation, partially expanded. FIG. 11C shows the device in a expanded state. The white arrows with black borders indicate the direction of movement of the sheath (FIG. 11B) and the activation tube (FIG. 11C).

Figure 12:
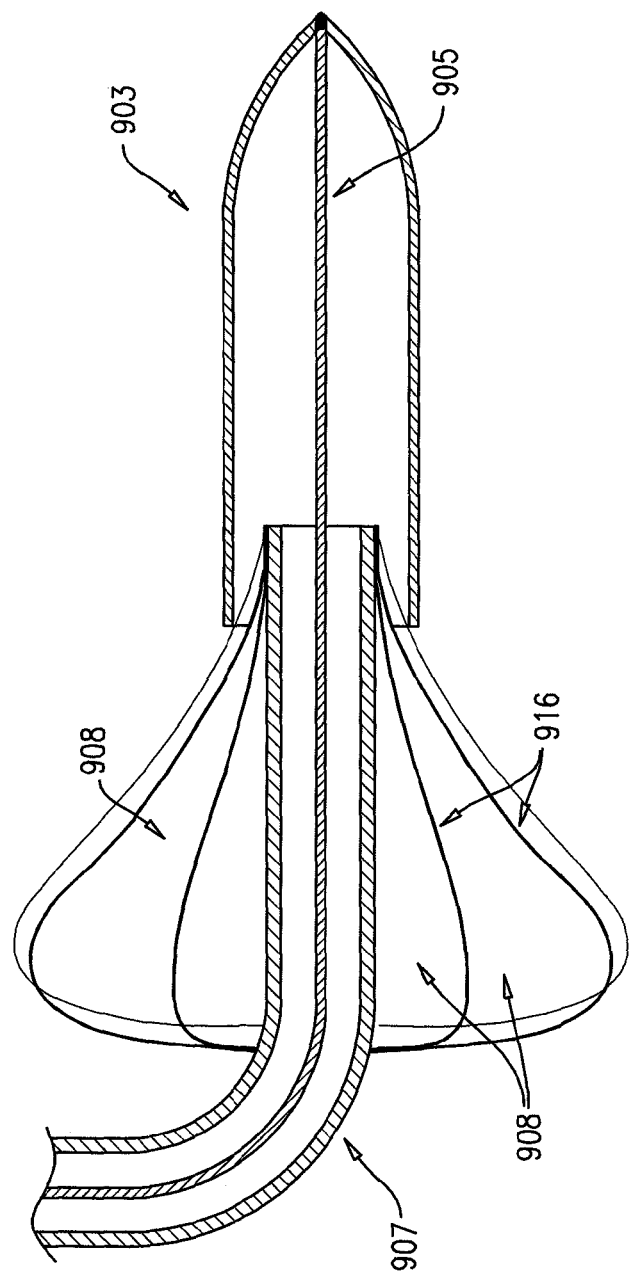

FIG. 12 is a schematic cross-sectional view of a device of the invention, including a cylindrical sheath (903), activation tube (907), filter leaflets (908), and an expanding element (916), in an expanded state.

Figure 13A:
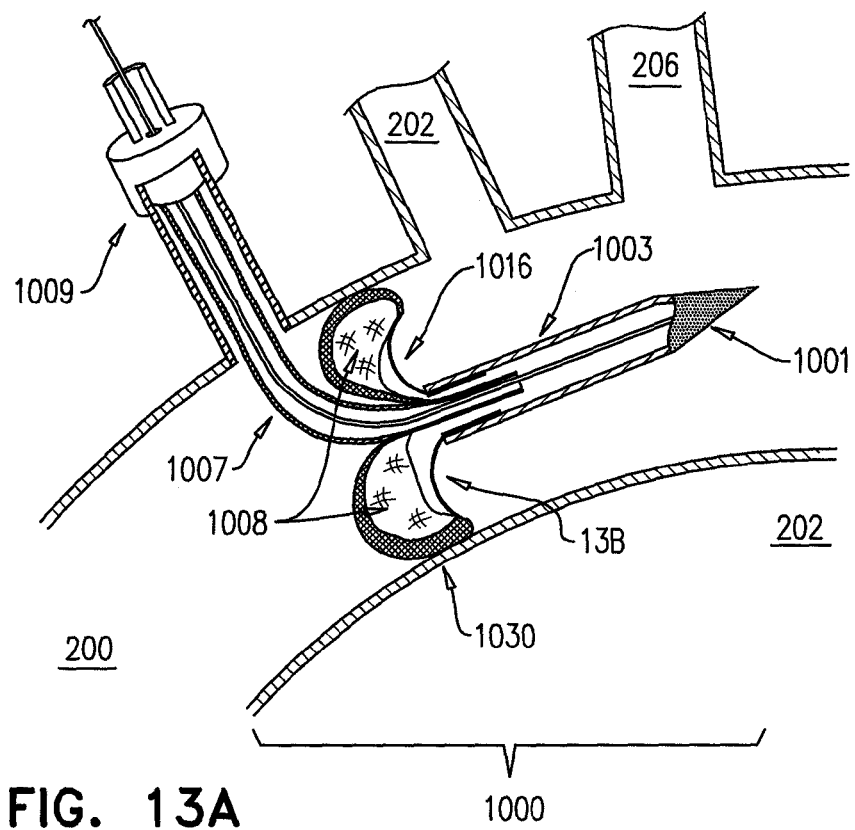
Figure 13B:
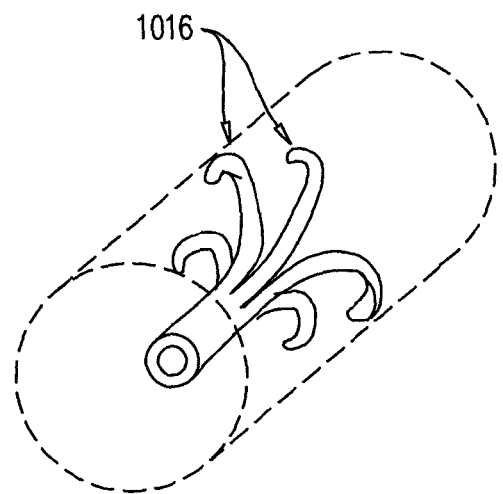

FIGS. 13A and B are cross-sectional or partially transparent schematics of a device of the invention including a cylindrical sheath (1003), activation tube (1007), and an expanding element (1016), in which the device is installed in a vascular system (e.g., an aorta), including an introducer cartridge (1009). FIG. 13A is a cross-sectional view of the device installed in an aorta between the ascending aorta (200) and the aortic arch (202). Also shown in FIG. 13A is an introducer cartridge (1009) for insertion of the device into the vascular system. The device is shown in an expanded state, including having formed a seal (1030) between the aortic walls and a filter leaflet (1008). FIG. 13B shows a partially transparent schematic of the expanding elements each of which is attached to the sheath (1003) by the proximal end of the elongated element (1016).

Figure 14A:
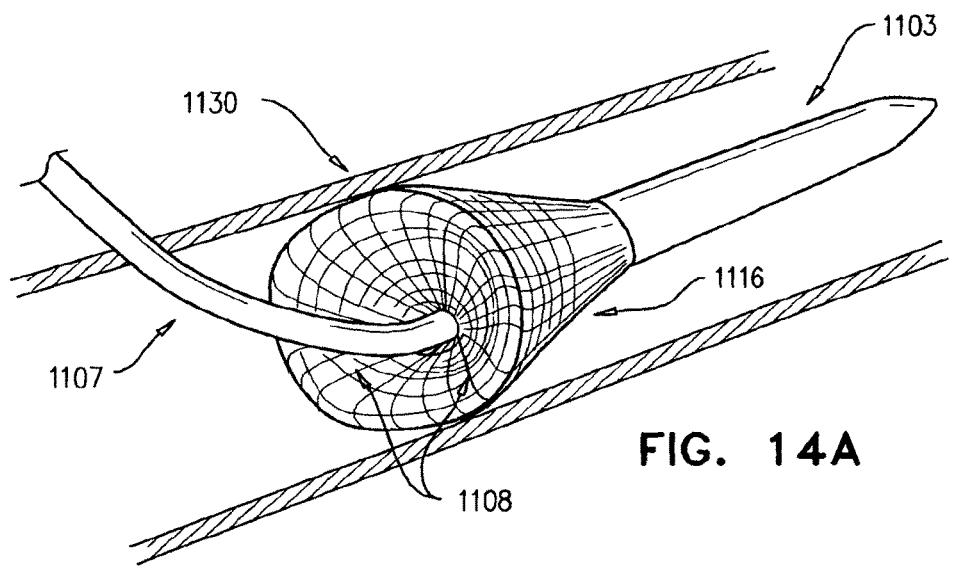
Figure 14B:
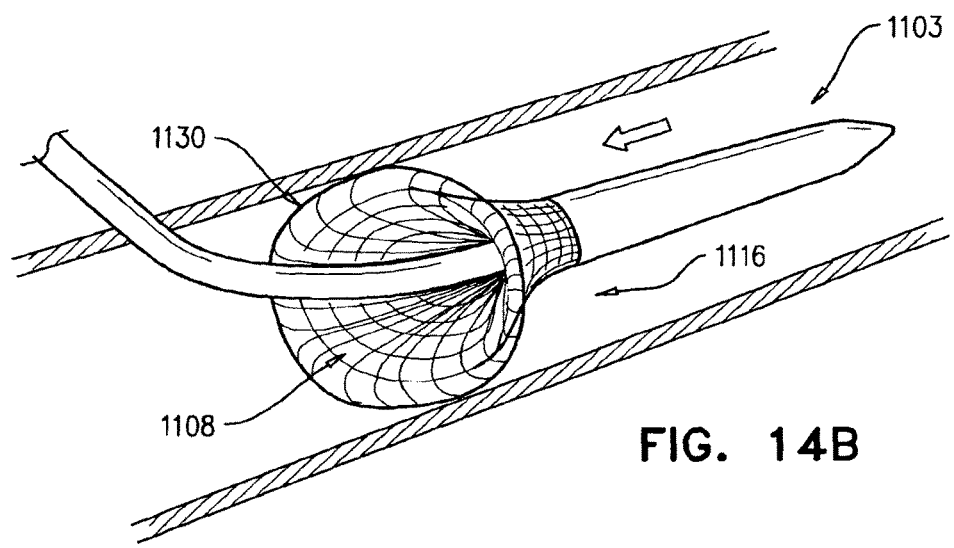

FIGS. 14A and 14B are schematics of a device of the invention including a cylindrical sheath (1103), activation tube (1107), and an expanding element (1116) installed in a vascular system. The white arrow with a black border shows the direction of movement of a sheath to reduce the diameter of a expanded filter for placement of the filter into smaller diameter vascular systems.

Figure 15A:
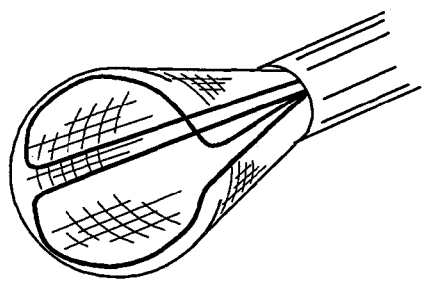
Figure 15B:
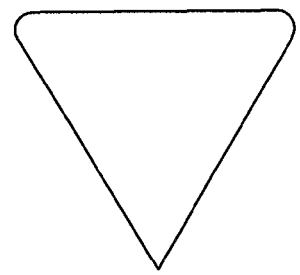
Figure 15C:
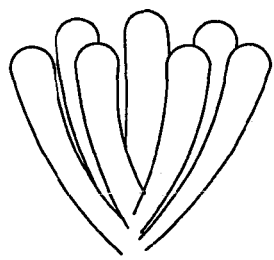
Figure 15D:
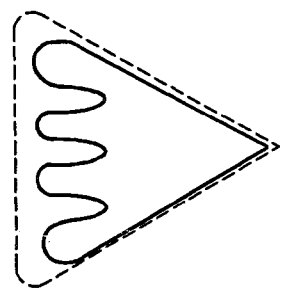
Figure 15E:
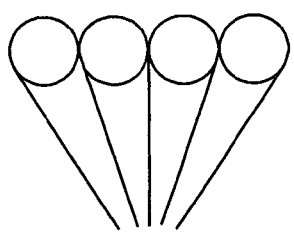
Figure 15F:
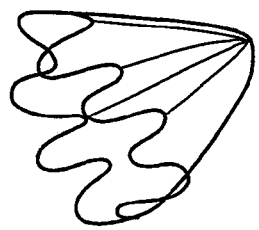

FIGS. 15A-15F are schematics of different expanding element configurations of the invention. FIG. 15A shows two planar, hemisphere expanding elements. FIG. 15B shows a planar, triangular expanding element. FIG. 15C shows multiple curved expanding elements. FIG. 15D shows multiple cone like expanding elements. FIG. 15E shows a planar expanding element with an undulating edge. FIG. 15F shows two planar expanding elements with undulating edges forming a "clam shell" like structure.

Figure 16B:
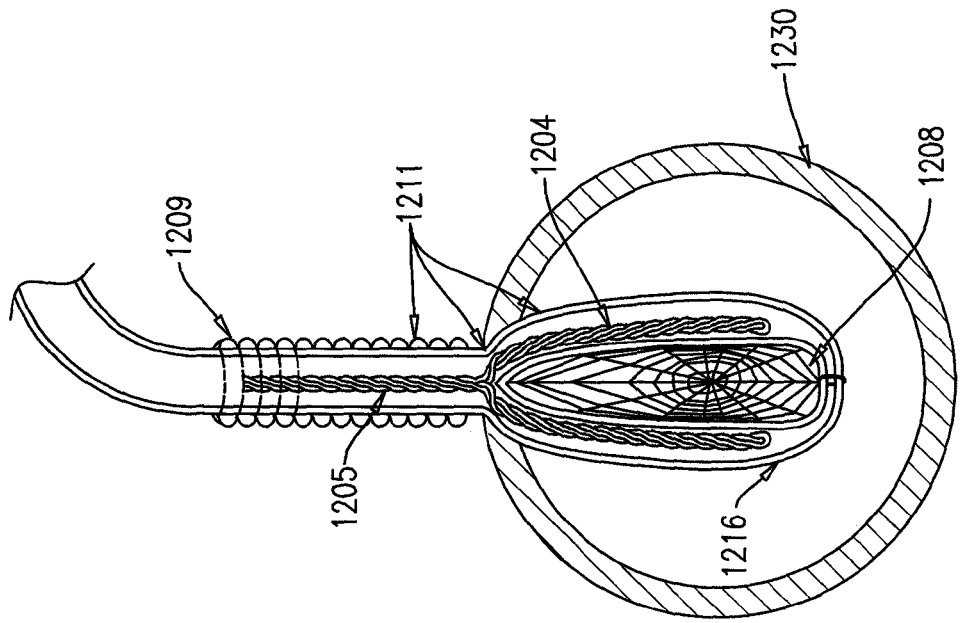
Figure 16A:
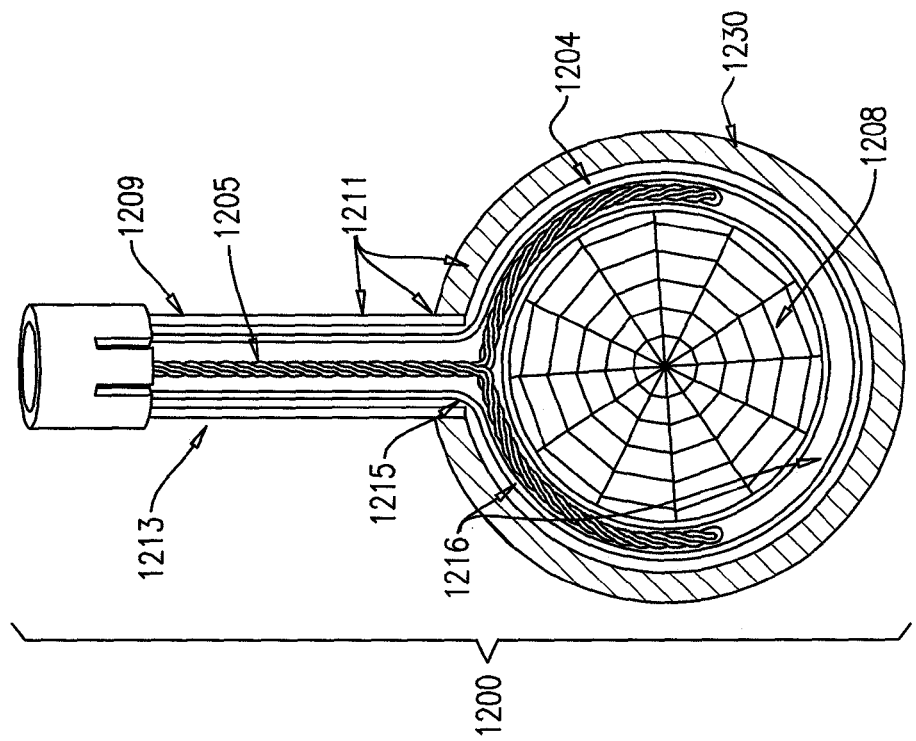

FIGS. 16A and 16B are schematics of a device of the invention including an elongated wire (1205), an flexible tube (1211), two elongated members (1204), a filter (1208), and a loop region (1216). FIG. 16A shows the device in an expanded stated, the flexible tube forming a seal with a wall of a vascular system (1230). FIG. 16B shows the device in a collapsed (e.g., non-expanded) state within a vascular system.

Figure 17:
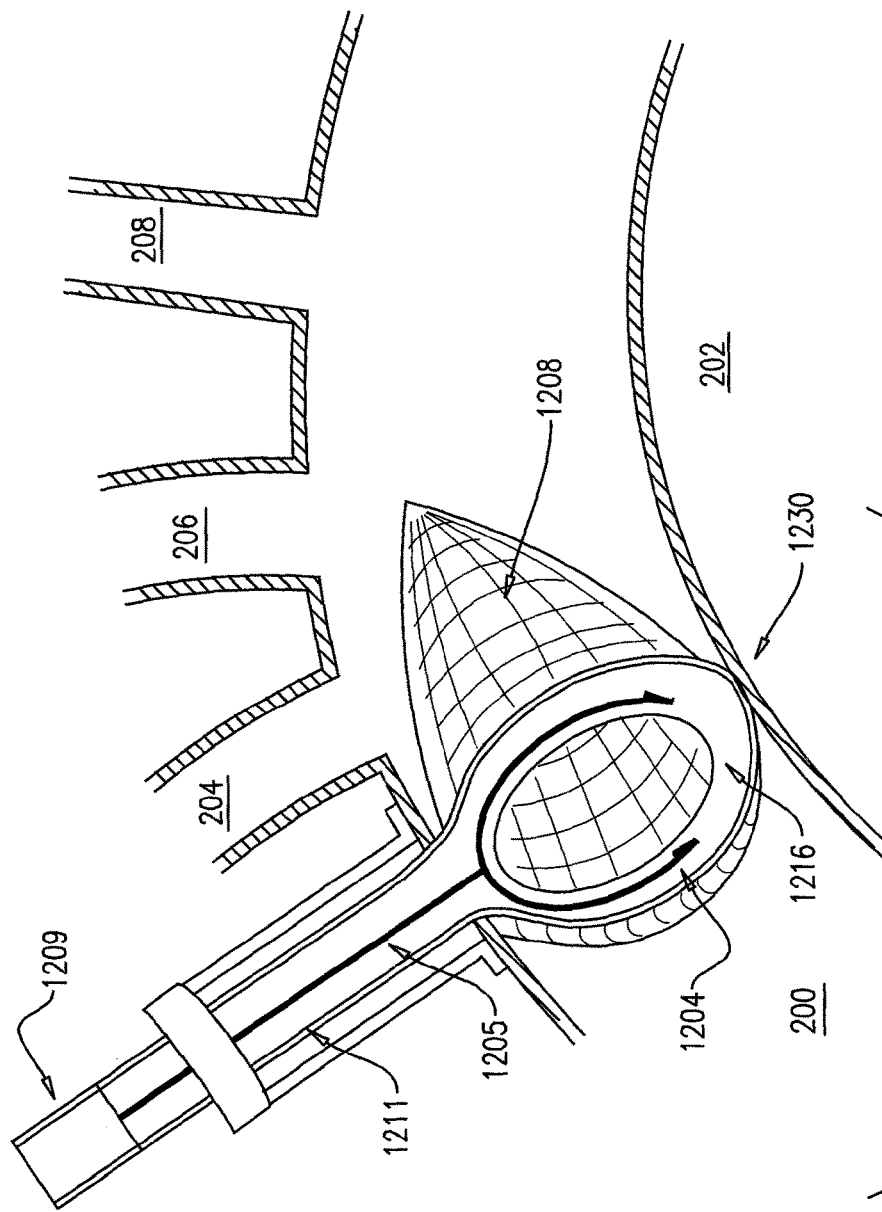

FIG. 17 is a schematic cross-sectional view of a device of the invention including an elongated wire (1205), elongated flexible tube (1211), two elongated members (1204), a loop region (1216), a filter (1208), and an introducer (1209) installed in an aorta between the ascending aorta (200) and the aortic arch (202).

Figure 18C:
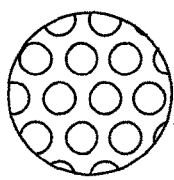
Figure 18D:
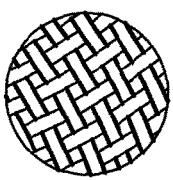
Figure 18E:
Figure 18F:
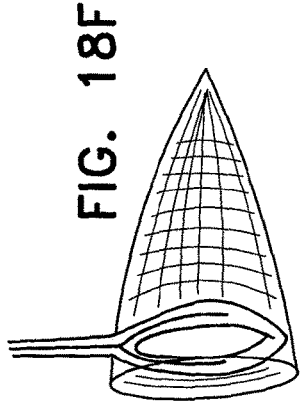
Figure 18B:
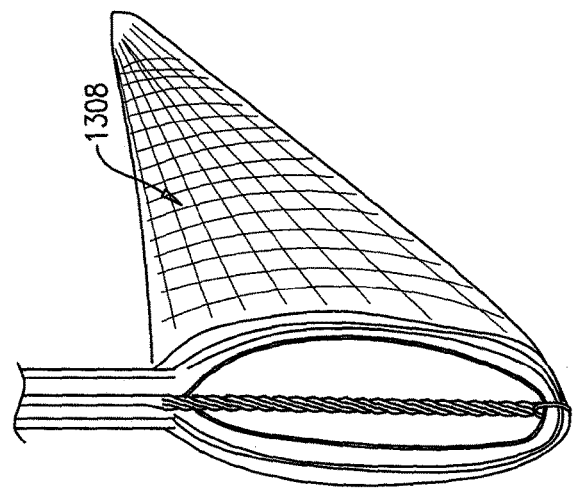
Figure 18A:
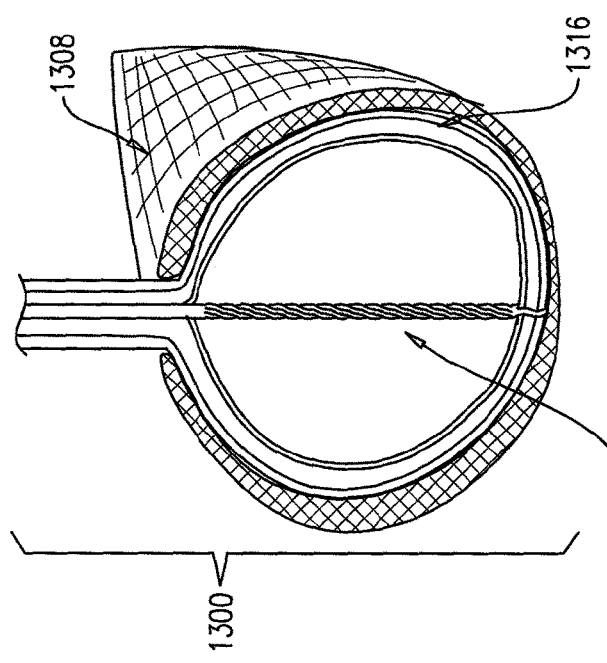

FIGS. 18A-18F are schematics of a device of the invention including an elongated wire (1304), an flexible tube including a loop region (1316), and a filter (1308). FIG. 18A shows a device of the invention in an expanded state in which the elongated wire (1304) spans the loop region providing mechanical support. FIG. 18B is a side view of the device showing the filter forming an apex of a mesh material and extending from the plane of the loop region. FIG. 18C shows an array of circular holes containing filter material or mesh pattern. FIG. 18D shows a woven filter material or mesh pattern. FIG. 18E shows another woven filter material or mesh pattern. FIG. 18F shows a filter material or mesh pattern extending in both directions (e.g., in front of and behind) the plane of the loop region of the device.

DETAILED DESCRIPTION

This invention relates to intravascular devices for the prevention of particulates, e.g., emboli and particles, from moving into a patients vascular system. In particular, the invention may include a frame and a filter which may be reversibly and robustly positioned in a vascular system, thus intercepting particulates potentially harmful to a subject. The intravascular device may be collapsed to fit within a delivery catheter. Once in position, the intravascular device may be reversibly expanded, installed, and stabilized using several features including, e.g., supporting elements, expanding elements, and/or stabilizing elements. The filter element may include several filter or mesh leaflets which may be reversibly collapsed and expanded.

In particular embodiments, the present invention provides one or more of the following advantages. First, the device and methods herein allow for the implantation of an intravascular device using a delivery catheter providing a minimally invasive procedure (e.g., device is foldable and self-deployable). Second, the filter captures particulate by collapsing the filter prior to removal from the subject. Third, the device may expand to provide a seal between the device and the vascular system wall, thus eliminating or reducing fluid bypass around the filter. Fourth, the expanding and stabilizing elements of the device may be activated by simple mechanical or pneumatic means. Fifth, the device allows direct approach into the ascending aorta to facilitate capture of particulates released during a procedure (e.g., an aortic cross clamp placement and removal; which clinical studies have shown contribute 66% of the emboli released, Barbut et. al., Cerebral emboli detected during bypass surgery are associated with clamp removal. Stroke 1994 December; 25(12):2398-402; incorporated as a reference herein). Finally, devices of the invention may include two or more filter leaflets, which provide access points between leaflets for surgical instruments and other medical devices.

Intravascular Filter Devices

Intravascular devices of the invention may be configured in many different ways as exemplified in the embodiments described herein. One critical function of the device may be the expansion of a filter to form a continuous filter surface occupying a cross-section of a vascular pathway in order to intercept particulates. The expansion of the filter may be accomplished through mechanical means using tension (supporting and expanding elements), compression (bending of a flexible element of a fixed length), or inflation (expansion with internal pressure). The expansion of the filter may eliminate or reduce fluid bypass of the filter material. For example, the expansion of a filter including multiple overlapping filter leaflets allows for compression of the filter leaflets against the vascular system walls (thereby forming a seal) and of the filter leaflets against an adjacent filter leaflet (thereby forming a seal between leaflets). Upon sealing the filter leaflets with the vascular wall and each other, the fluid flow is now directed through the filter material and fluid bypass is eliminated or reduced. Expansion of the filter also may play a critical role in delivery of the device. In the collapsed or non-expanded state, devices of the invention may be configured into delivery catheters and other devices which facilitate implantation or installation into a vascular system.

Devices with Supporting and Expanding Elements

Figure 2:
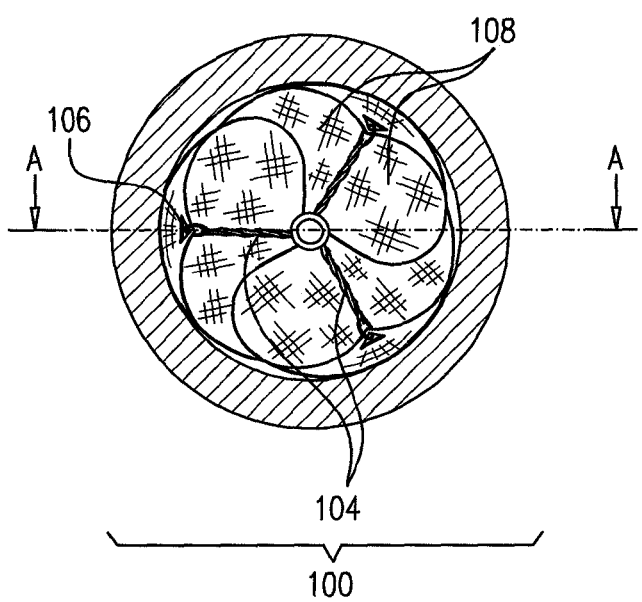
FIG. 2 is a schematic diagram of a view of an exemplary intravascular device of the invention (100) along the line A-A of FIG. 1. The diagram shows three supporting elements (104), multiple, overlapping filter leaflets (108), and the first attachment portions (106) of the leaflets attached to the supporting elements.

In particular embodiments, intravascular device 100 (FIG. 1 and FIG. 2) includes first end 102 and second end 112, multiple supporting elements 104, and several filter leaflets 108. Filter leaflets 108 are connected to supporting elements 104 with attachment portion 106. Filter leaflets 108 are connected to second end 112 by second attachment portions 110 of the filter leaflets 108. The overlapping filter leaflets 108 form a continuous filter surface (FIG. 2) which is held open by a combination of supporting elements 104 and expanding elements attached to a central elongated wire. Supporting element 104 provides retention of the filter leaflet (e.g., tension) to counter expansion of the filter leaflets from fluid flow or a force from an expanding element.

Figure 3:
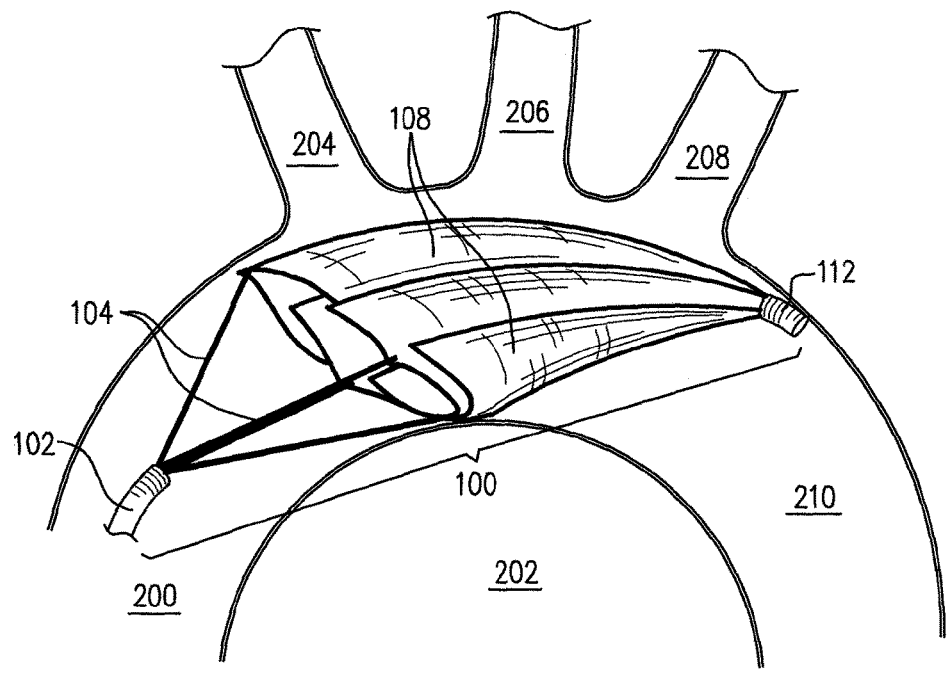
FIG. 3 is a schematic diagram of a cross-sectional view of an exemplary intravascular device of the invention implanted in an aortic arch. The diagram shows an intravascular device (100) installed in the aortic arch (202), with the filter leaflets (108) spanning the superior arteries of the aorta (e.g., the brachiocephalic artery (204), the left common artery (206), and the left subclavian artery (208)), beginning at the ascending aorta (200) and terminating at the descending aorta (210).

In some embodiments, intravascular filter 100 may be installed in aortic arch 202 (FIG. 3). First end 102 may be positioned in the region between aortic arch 202 and ascending aorta 200. Second end 112 may be positioned in the region between aortic arch 202 and descending aorta 210. Supporting elements 104 assist in maintaining an expanded structure such that filter leaflets 108 overlap to form a continuous filter surface and create a cone like geometry intercepting particulates, e.g., emboli, moving from ascending aorta 200 into aortic arch 202. In further embodiments, intravascular device 100 may be installed into aortic arch 202 such that particulates are prevented from entering brachiocephalic artery 204, left common artery 206, and left subclavian artery 208. Intravascular device 100 may include an elongated wire connected to first end 102, an expanding element sized and shaped to contact filter leaflets 108 and form a continuous filter surface, and second end 112. In further embodiments, at least one filter leaflet 108 may be attached to or contact the elongated wire.

Figure 4:
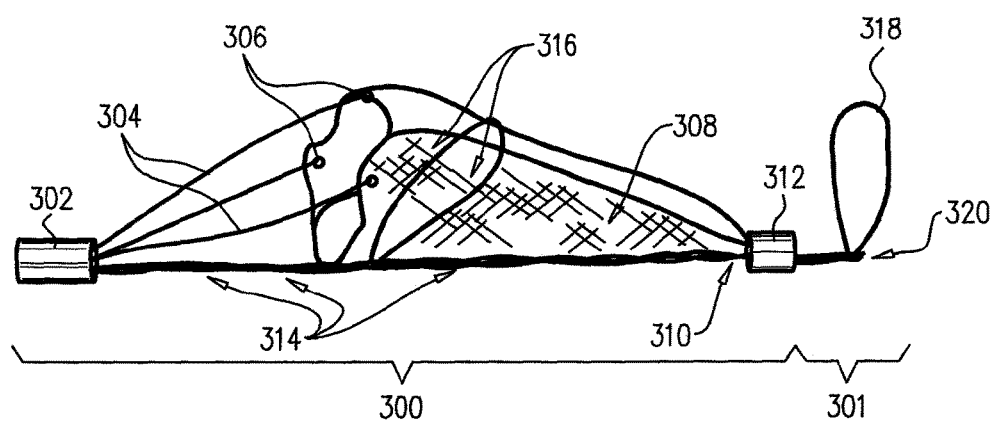
FIG. 4 is a schematic diagram of a cross-sectional view an exemplary intravascular device of the invention, including a secondary frame with a stabilizing element. A component of the primary frame (300), the expanding element (316), which is internal to the leaflets, is shown through a transparent section of the leaflet (308). The expanding element (316) extends away from the wire and contacts the filter leaflets, thus ensuring the filter is expanded and open. Secondary frame (301) includes stabilizing element (318) and is attached at second end (312) of elongated wire (314) to distal end of wire (320) of the secondary frame.

In some embodiments, intravascular device 300 has first end 302 connected to second end 312 by elongated wire 314 (FIG. 4). Supporting elements 304 are connected to first end 302 and multiple filter leaflets 308 by leaflet first attachment portions 306. Filter leaflets are attached to second end 312 by second attachment portion 310. Filter leaflets 308 are expanded by a combination of expanding element 316 (e.g., a loop) and supporting elements 304 (e.g., a cord, chain, or wire). Expanding element 316 is within filter leaflets 308 and anchored to elongated wire 314. Expanding element 316 may be reversibly collapsed or expanded by twisting elongated wire 314 or other controllable means. Elongated wire 314 contacts and/or passes through stabilizing element 318, second end 312, filter leaflets 308, supporting elements 304, and terminates at first end 302. In other embodiments, intravascular device 300 includes secondary frame 301. Secondary frame 301 includes stabilizing element 318 (e.g., a loop) and elongated wire 320. Stabilizing element 318 is attached to elongated wire 320. Stabilizing element 318 may be reversibly collapsed or expanded by twisting elongated wire 320 or other controllable means.

Figure 5:
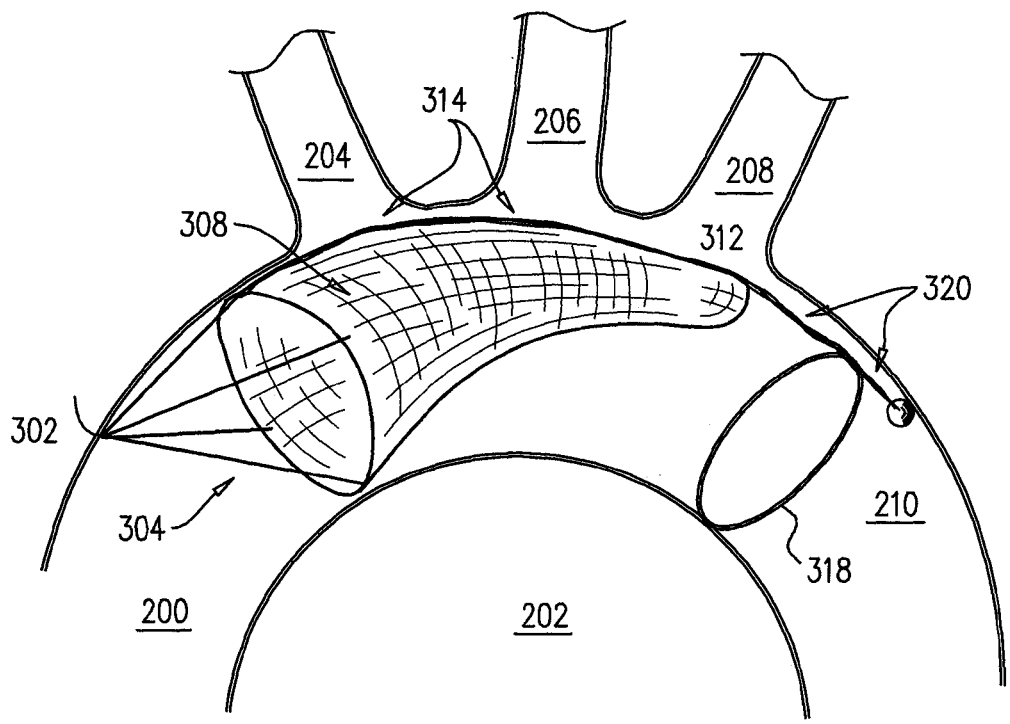
FIG. 5. is a schematic diagram of a cross-sectional view of an exemplary intravascular device of the invention, including a secondary frame, implanted in an aortic arch.

In some embodiments, intravascular device 300/301 may be installed in aortic arch 202 (FIG. 5). First end 302 may be positioned in a region between ascending aorta 200 and aortic arch 202. First end 302 may include an anchoring feature to contact the superior surface of a region between ascending aorta 200 and aortic arch 202. Elongated wire 314 may contact a surface of the region between ascending aorta 200 and aortic arch 202, brachiocephalic artery 204, left common artery 206, left subclavian artery 208, and a the region between descending aorta 200 and aortic arch 202. Filter leaflets 308 may be expanded by internal expanding element 316 (not shown in FIG. 5) and supporting elements 304. Filter leaflets 308 form an overlapping, continuous filter surface. The intravascular filter may be positioned to prevent particulates from entering brachiocephalic artery 204, left common artery 206, left subclavian artery 208, and descending aorta 200. Stabilizing element 318 may be expanded to contact the superior and inferior surfaces of the region between aortic arch 202 and descending aorta 210, thus providing an anchor point preventing rotation or movement of the intravascular filter 300/301.

In further embodiments, filter leaflet 408 has first attachment portion 406, supporting element 404, and a second attachment portion 410 (FIG. 6A). Multiple filter leaflets 408 may be assembled into a filter (FIG. 6B) having a continuous filter surface having multiple supporting elements 404 (e.g., one supporting element for each filter leaflet), multiple first attachment portions 406 (e.g., one first attachment portion for each filter leaflet), and multiple second attachment portions 410 (e.g., one second attachment portion for each filter leaflet).

In some embodiments, the expanding element and/or the stabilizing element is a wire or fiber attached to the elongated wire 314. For example, the expanding element and/or stabilizing element may be expanded wire loop 516 (FIG. 7A). The expanded wire loop 516 may provide a force to expand a filter leaflet (e.g., be an expanding element) or provide an anchoring point within a vascular system (e.g., be a stabilizing element). Expanded wire loop 516 may be collapsed by twisting the elongated wire connected the expanding or stabilizing element. Upon twisting the expanded wire loop (e.g., in a counter clockwise direction), the loop will contract (FIG. 7B). After further twisting, the expanded wire loop will collapse on to itself, forming folded loop 517 and reducing the loops overall length (FIG. 7C).

Devices with Combined Supporting and Expanding Elements

In yet another embodiment, the invention features a supporting element and an expanding element may be combined into a expanding element. For example, device 600 has expanding element 616 having a distal end 603, proximal end 605, and an intervening portion 607 which is attached to first attachment portion 606 of filter leaflet 608 (FIG. 8B), thus expanding element 616 functions as an expanding element and a supporting element. Distal end 603 of expanding element 616 may be attached to first end 602. Proximal end 605 of expanding element 616 may be attached to second end 612 of elongated wire 614. Second attachment portions 610 of filter leaflets 608 are attached to second end 612. Expansion of expanding elements 616 is activated by movement of first end 603 along elongated wire 614 relative to second end 612. In a collapsed state (device 601, FIG. 8A) expanding elements 616 are parallel to elongated wire 614 (leaflets 608 would also be collapsed, but are not shown in FIG. 8A for clarity). Upon activation by moving distal end 603 towards second end 612, intervening portion 607 of expanding element 616 bends and is deflected away from elongated wire 614 (FIG. 8B) and leaflets 608 are expanded. The expanded leaflets may contact and seal against the surface of an aorta, thus installing expanded intravascular device 600. Leaflets 608 may have a shape including edges with a 45 degree angle in order to allow for better folding and reducing collapsed leaflet volume. The expansion may be controlled by the amount of deflection resulting from the movement of distal end 603 relative to second end 612. For example, the height (h) or the distance of the deflection of the apex of expanding element 616 from elongated wire 614 depends on the distance (a) between distal end 603 and the apex of intervening portion 607 of expanding element 616 (FIG. 8C). The length(s) of expanding element between the apex and distal end 603, is longer than the distance a. The movement of distal end 603, causes the apex of expanding element 616 to move away from elongated wire 614, thus increasing the height (h). Expanding elements 616 may be actuated all together simultaneously or each element individually.

In some embodiments, an intravascular device 700 may have an expanding element 716 may be, e.g., a planar triangular or propeller structure. For example, first end 702 may be configured to allow one or more expanding elements 716 to extend past and rest parallel to elongated wire 714 (dashed lines of FIG. 9B). One or more filter leaflets 708 may be attached to expanding element 716 (FIG. 9A). When expanding element 716 is move perpendicular to elongated wire 714 (FIGS. 9A and 9B), filter leaflets 708 are expanded away from elongated wire 714. Devices including expanding elements 616 and 716 may be collapsed to be configured essentially parallel to an elongated wire (FIGS. 10A to 10C, filter leaflets not shown). The collapsed configuration allows for incorporation into a delivery catheter or delivery device.

Devices with a Sheath Element

In another embodiment, an intravascular device 900 may include a sheath 903 configured to encompass an elongated wire 905, one or more expanding elements 916, filter 908, and activation tube 907. Expanding elements 916 have distal end 909, proximal end 911, and intervening portion. Distal end 916 is attached to first attachment portion 906 of filter leaflet 908. Proximal end 911 is attached to sheath 903. Filter leaflet 908 has second attachment portion 910 attached to the distal end 913 of activation tube 907. During insertion into a vascular system, device 900 may be in a non-expanded state with sheath 903 containing one or more filter leaflets 908 (FIG. 11A). Once device 900 is in position, sheath 903 may be moved away from activation tube 907 using elongated wire 905 (FIG. 11B). As sheath 903 moves, expanding element 916 may expand. In this manner, the diameter of filter leaflet 908 may be controlled as the extension of filter leaflet 908 is proportional to expansion of expanding element 916 to which it is attached. In addition, activation tube 907 may also be moved to deploy filter leaflet 908 (FIG. 11C). In another embodiment, the intravascular device may include filter leaflets 908 and expanding element 916 attached to activation tube 907 (FIG. 12).

In another embodiment, an intravascular device may be installed in a vascular system, expanding elements 1016 provides a force to seal filter leaflet 1008 against a surface of the vascular system 1030 (FIG. 13A), thus eliminating or reducing fluid bypass of filter leaflet 1008. Device 1000 may include one or more filter leaflets 1008 or a single circumferential filter. Device 1000 may include a sheath 1003 with a pointed end 1001. The diameter of filter leaflets 1008 or the filter may be controlled by the position of sheath 1003 relative to expanding elements 1016 (FIG. 13B). Sheath 1003 may restrain expanding elements 1016. Therefore, the diameter of the filter leaflets or the filter is proportional to the extent to which expanding elements 1016 are not contained by sheath 1003. In this manner, the diameter of filter leaflets 1008 on a single filter may be controlled and sized appropriately for installation into a vascular system. Device 1000 may also installed using an introducer or introducer cartridge 1009. Introducer 1009 allows for more stable and efficient maneuvering and installation of device 1000. Device 1000 may be installed between ascending aorta 200 and aortic arch 202, thus preventing particulates (e.g., emboli or a particle) from entering vascular components such as brachiocephalic artery 202 and/or left common carotid artery 206.

In an additional embodiment, a device having a sheath 1103, activation tube 1107, expanding element(s) 1116, and filter 1108 may be installed in a vascular system (FIG. 14A). A seal between filter 1108 and the vascular surface 1130 prevents fluid bypass. The device may be moved, repositioned, or reinstalled without removal of the device from the vascular system by contracting filter 1108 and expanding elements 1116 thus releasing the seal to intravascular surface 1130. The contraction of filter 1108 and expanding elements 1116 may be accomplished by the movement of sheath 1103 towards activation tube 1107 (white arrow, FIG. 14B), thereby suppressing the extension of expanding elements 1116.

In yet other embodiments, the expanding elements may be two planar, hemisphere expanding elements (FIG. 15A), planar, triangular expanding element (FIG. 15B), multiple curved expanding elements (FIG. 15C), multiple cone like expanding elements (FIG. 15D), planar expanding element with an undulating edge (FIG. 15E), or two planar expanding elements with undulating edges forming a "clam shell" like structure (FIG. 15F).

Devices with Inflatable Expanding Elements

In some embodiments, device 1200 includes elongated wire 1205, a flexible tube 1211, two elongated members 1204 (which may be integral with wire 1205), a filter 1208. Flexible tube 1211 includes a linear region 1213, a branch region 1215, and a loop region 1216. Elongated wire 1205 and elongated members 1204 provide support for the structure during installation, before inflation (FIG. 16B), and after inflation (FIG. 16A). Flexible tube 1211 may be configured to be pressurized and contains elongated wire 1205. Tube 1211 is attached to loop region 1216 which is also configured to be pressurized. Loop region 1216 may be configured with a material (e.g., silicon, Pebax®, or other compliant materials) and a shape or size to expand and make contact with a vessel surface 1230 (e.g., an aortic surface). In this manner, loop region 1216 may form a seal with vascular surface 1230 this eliminating or reducing bypass of fluid around filter 1208. Appropriate materials and tube diameters/sizing may be determined by a compliance chart, which includes loop region 1216 diameter compared to the internal pressure applied (e.g., provides predictive understanding of device size and pressure required to deploy device in a given anatomy). A single device configuration may be used to fit a range of intravascular systems (e.g., the diameter of loop region 1216 may be tuned by adjustments of the internal pressure). Device 1200 may include an inducer attachment 1209 to facilitate installation of the device. Ultrasonic contrast medium in a liquid may be used to pressurize loop region 1216. This embodiment adds the advantage of being able to more easily see the device using ultrasound to monitor the procedure.

In another embodiment, device 1200 is installed in a region between ascending aorta 200 and aortic arch 202 (FIG. 17). Device 1200 may be inflated and loop region 1216 forms a seal with intravascular wall 1230. Blood flow from the ascending aorta passes through filter 1208, thus preventing particles (e.g., emboli) from reaching superior arteries 204, 206, and 208. Introducer 1209 may aid or improve installation of device 1200.

In yet another embodiment, device 1300 may include an elongated wire 1304 which extends across and supports loop region 1316 (FIG. 18A). Filter 1308 extends out of the plane of flexible tube 1316 coming to an apex (FIG. 18B). Device 1300 may have filter mesh of different pore sizes and constructions, including an array of circular holes (FIG. 18C), a woven filter (FIG. 18D), and a woven filter with small pores (FIG. 18E). In some embodiments, a filter mesh may extend in both directions (e.g., in front of and behind) from the plane of the flexible tube loop region (FIG. 18F).

In any of the above embodiments, a supporting element may be a wire, chain, fiber, rod, loop, or another structure capable of supporting a filter leaflet under tension from fluid flow or and expanding element. A supporting element may be mechanically attached to the first end of the intravascular device (e.g., first end 102 or 302, FIGS. 1 and 4) by mechanical means (e.g., a crimp, compression fit, lock and key fit, or clamping), an adhesive, and/or thermal bonding (e.g., welding metal to metal, soldering, or melting plastic to plastic). A supporting element may be coated with an anti-thrombogenic coating. In some embodiments, a supporting element may be constructed from a single continuous wire.

In some embodiments, the expanding elements and or stabilizing elements may be wire, chain, fiber, rod, loop, tube, or another structure capable of supporting a filter leaflet. A expanding element may be mechanically attached to the elongated wire of the intravascular device (e.g., 314, FIG. 4) by mechanical means (e.g., a crimp, compression fit, lock and key fit, or clamping), an adhesive, and/or thermal bonding (e.g., welding metal to metal or melting plastic to plastic). An expanding element may change dimensions and/or shape in a controlled manner, induced from an external input. For example, the elongated wire may be rotated, thus inducing the expanding member to twist and collapse or expand. In a preferred embodiment, the expanding element is a wire loop affixed to the elongated wire by mechanical means. The expanding element may be collapsed by twisting the elongated wire, e.g., counter-clockwise, thus folding the loop on to itself (FIG. 7A to 7C). Once the intravascular device is in the proper location within the patient's heart, the elongated wire can be twisted, e.g., clockwise, thus unfolding the wire loop. The loop contacts the filter leaflets, thus pushing them away from the elongated wire. The wire loop rests against the filter leaflets and maintains the cone like structure of the expanded filter leaflets. A device may include one or more, two or more, three or more, four or more, five ore more, six or more, 10 or more, 20 or more, 50 or more, or 100 or more expanding elements, supporting elements, or stabilizing elements. An expanding element may be coated with an anti-thrombogenic coating. In some embodiments, an expanding element may be constructed from a single continuous wire.

In some embodiments, a filter, filter leaflet or a filter material may be in the form of a mesh, porous sheet, woven, non-woven, partially knitted material, single layer, multiple layers, array of circular holes, netting, fine wire mesh, perforated film, or membrane. Filter material may be a polymer, plastic, metal, flexible metal (e.g., nitinol), stainless steel, cobalt-chromium alloy, nylon, cloth, shape memory material, biocompatible polymer, or superelastic material. A filter may be a series of overlapping leaflets, a single layer, or multiple layers. The filter may have a single pore size, multiple pore sizes in a single layer, or multiple pore sizes in multiple layers. In some embodiments, filter pore sizes range from 50 to 1000 µm. In more preferred embodiments, filter pore size ranges from 100 µm to 500 µm (e.g., 100 to 500 µm, 200 µm to 500 µm, 300 µm to 500 µm, 400 µm to 500 µm, 100 µm to 400 µm, 100 µm to 300 µm, 100 µm to 200 µm, 200 µm to 400 µm, 200 µm to 300 µm, 300 µm to 400 µm). In other embodiments, a filter may have a pore size less than 300 µm. A filter may include two or more, three or more, four or more, five ore more, six or more, 10 or more, 20 or more, 50 or more, or 100 or more leaflets. A filter may be symmetric or asymmetric. A filter may be coated with an anti-thrombogenic coating.

In some embodiments, a device of the invention may have a filter leaflet including a first attachment portion of a filter leaflet includes an eyelet, tab, hole in filter material, grommet, clasp, hook, crimp or a fastener. In other embodiments, a filter leaflet may be attached to a supporting element or expanding element with an adhesive, glue, soldering, or heat bonding (e.g., melting material together). A filter leaflet may include two or more, three or more, four or more, five ore more, six or more, 10 or more, 20 or more, 50 or more, or 100 or more attachment portions.

In some embodiments, a device of the invention includes an elongated wire which may be a tube or have an internal channel. In this embodiment, providing a connection of the interior channel to the exterior of the wire or tube (e.g., an aspiration port) may allow for the aspiration of particles in regions of an intravascular device adjacent to the elongated tube or wire. For example, providing an aspiration port in wire 314 adjacent to second end 312 (FIG. 4) facilitates aspiration of particulates collected by filter leaflets 308. In this manner, intravascular device 300 could be used for a longer period of time (e.g., remove more particulates) without becoming plugged. In addition, this embodiment allows for an access port to sample blood in the vascular system for diagnostic and other purposes.

In some embodiments, a device of the invention includes an introducer (e.g, introducer 1009, FIG. 13A; introducer 1209, FIGS. 16A and 17). In this embodiment, the introducer includes a valve which may be configured to ensure the intravascular device is installed with the filter in the proper orientation (e.g., filter extends into the aortic arch, not the ascending aorta). In addition, the introducer may minimize blood loss by providing a valve to isolate the intravascular system as required.

In some embodiments, a device may have one or more supporting elements, expanding elements, stabilizing elements, filter leaflets, filters, elongated wires, activation tubes, expandable circular tubes, flexible tubes, introducers, elongated members, sheaths. Combinations of these elements and features may be configured to further stabilize, activate, position a device of the invention or provide filtration to multiple locations using a device of the invention.

Materials

Devices and aspects of the invention may be made with any useful material. Exemplary materials which may be used to fabricate devices of the invention include materials used in medical devices, metals (e.g., platinum, tantalum), stainless steel, polymers and plastics, metal alloys (e.g., nitinol), ceramics, silicones, composites and other biocompatible materials.

Exemplary elongated wire materials which may be used include metals, metal alloys (e.g, nitinol, zirconium alloys, and cobalt chromium alloys), plastics (e.g., polyethylene, ultra high molecular weight polyethylene, and polyether ether ketone), polymers, ceramics, and composites thereof.

Supporting elements, expanding elements, and/or stabilizing elements may be constructed of the same or different materials. Exemplary materials include metals, metal alloys (e.g, nitinol, zirconium alloys, and cobalt chromium alloys), shape memory material, superelastic materials, plastics (e.g., polyethylene, ultra high molecular weight polyethylene, and polyether ether ketone), polymers, and composites thereof. Most preferably the material is flexible or ductile to facilitate folding or bending.

Exemplary filter materials which may be used include: a polymer (e.g., polycarbonate, polytetrafluoroethylene (PTFE), expanded polytetrafluoroethylene (ePTFE), polyvinylidene fluoride (PVDF), polypropylene, porous urethane, para-aramid (Kevlar®)), plastic, metal, flexible metal (e.g., nitinol), stainless steel, cobalt-chromium alloy, nylon, cloth, shape memory material, biocompatible polymer, or superelastic material. A filter material may have a pore size of 50 microns (µm) to 1000 µm. A filter material may have a pore size between about 100 µm to about 500 µm. A filter material may have a pore of less than 300 µm.

Filters of the invention may contain one or more access ports (see description in U.S. Pat. No. 7,232,453; herein incorporated as a reference in its entirety). Access ports may be at one end of a filter, provided by a catheter to which the filter or filter leaflets are attached, and/or on the side of a filter or filter leaflet.

Exemplary materials which may be used for inflatable expanding elements include silicon, Pebax®, polyethylene, copolymers of polyethylene, polytetrafluoroethylene, or other compliant materials.

Exemplary materials which may be used to adjust the pressure inside a flexible tube include gas (e.g., compressed air, nitrogen or argon), liquid, vapor, liquid containing an ultrasound contrast medium, buffers, or saline solution.

Methods of Use

Intravascular devices of the invention may be collapsed, contained in a delivery device, and installed in a vascular system. Installation can be trans-catheter (transarterial) or by direct access. Exemplary transarterial access includes transfemoral (in the upper leg), transapical (through the wall of the heart), subclavian (beneath the collar bone), and direct aortic (through a minimally invasive surgical incision into the aorta). Installation may involve one or more delivery catheters, one or more guide wires, and/or delivery devices. Device components, including supporting elements, expanding elements, filters, and/or stabilizing elements may be folded, compressed, or otherwise manipulated to be inserted into a delivery device (e.g., a delivery catheter). The delivery device may be inserted into a subject and positioned in a desired location. Once in position, the intravascular device may be removed from the delivery device. Components of the intravascular device may expand spontaneously or require activation (e.g., being pressurized) and/or manipulation (e.g., twisting of a delivery or operational catheter) to be expanded. The expansion of the frame generally expands the filter or filter leaflets. In some embodiments, the filter or filter leaflets may be expanded by blood flow or mechanical manipulation (e.g., catheter end used to expand filter or filter leaflets. The intravascular device may be moved into final position, before expansion is complete, during expansion, or after expansion is complete. Expansion of the intravascular device may seal the device with one or more surfaces of the vascular system. In some embodiments, a device of the invention is partially expanded and moved into position, then expanded to seal the device within the vascular pathway (e.g., sealed within the region between the ascending aorta and the aortic arch).

Once installation has been completed, the device may be accessed by one or more surgical instruments (e.g., such as an ablation catheter, stent installation catheter, transarterial valve replacement or insertion apparatus, or other medical device). In general, filters of the invention allow for access of a surgical instrument through an access port, between filter leaflets, or an internal channel of a catheter to which the filter or filter leaflets are attached. During the procedure, any particulate dislodge or created may be intercepted by the filter, thus stopping particulates from entering the subject's vascular system. Once the procedure is complete, the surgical instruments may be removed and the intravascular device of the invention collapsed. The collapse of the intravascular device may include trapping one or more particulates in the filter (e.g., filter is collapsed rapidly to prevent particulates from diffusing into the vascular system). The collapsed device may be inserted back into a delivery device (e.g., a delivery catheter) and then removed from a subject.

In some embodiments, installation of a device of the invention requires removal of a sheath containing expanding elements. In this embodiment, the diameter of the expanded filter and expanding elements may be controlled by the degree in which the sheath has been removed. For example, a device of the invention may be expanded to seal within a large diameter vascular pathway (e.g., an artery). A device of the invention may be moved to seal within a smaller vascular pathway (e.g., a blood vessel with a diameter smaller than an artery) by applying the sheath, thus reducing the diameter of the filter and expanding elements, and moving the intravascular device to a new location. The device may be reinstalled by removing the sheath, thus allowing expansion of the filter and expanding elements, and creating a seal between the device and surfaces of the new location in the vascular system.

In yet further embodiments, one or more combinations of intravascular devices of the invention may be used to prevent particles from moving into a subject's intravascular system. For example, a device with inflatable expanding elements may be used in a second location (e.g., artery in leg of a subject) during a procedure at a first location (e.g., a subject's aorta) in which a device of the invention with supporting and expanding elements is being used to prevent particulates (e.g., an emboli) from moving into a subject's vascular system.

OTHER EMBODIMENTS

In still other embodiments, devices of the invention may be adapted for use with other particle and/or embolism protection devices (e.g., those described in U.S. application Ser. Nos. 13/300,936, 61/714,401, and 13/205,255; in U.S. Publications Nos. 2008/0255603 and US 2011/0106137; and U.S. Pat. Nos. 8,062,324 and 7,232,453; PCT Patent Application No. PCT/IL2012/000208), each of which is hereby incorporated by reference in its entirety. All publications, patent applications, and patents mentioned in this specification are herein incorporated by reference.

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention are intended to be within the scope of the invention.

What is claimed is:

1. An intravascular device to prevent a particle in the aorta from passing into a second blood vessel, said device comprising:
   a. a primary frame comprising:
      i. an elongated wire having a first end and a second end,
      ii. two or more supporting elements, each of said supporting elements attached to said first end of said wire, and
      iii. at least one expanding element attached to said wire between said first end and said second end and configured to reversibly extend away from said wire,
   b. a filter comprising:
      i. a distal end and a proximal end, and
      ii. two or more leaflets, each of said leaflets comprising a first attachment portion, a second attachment portion, and a filter material having pores which are both large enough to allow blood to pass through and small enough to prevent a particle from passing through said filter,
   wherein said supporting elements are attached to said first attachment portion of said leaflets and define the distal end of said filter, said second end of said wire is attached to said second attachment portion of said leaflets and define said proximal end of said filter, each of said two or more leaflets are configured to overlap with an adjacent leaflet to form a continuous filter surface, and said expanding element is configured to contact and support said filter upon expansion; such that when said intravascular device is deployed in an aortic arch, said elongated wire contacts a superior surface of said aortic arch, said distal end of said filter expands to fill the aorta and said proximal end of said filter converges to an apex, thereby preventing the bypass of fluid around said filter material and preventing a particle in the aorta from passing into a second blood vessel.

2. The device of claim 1, wherein said expanding element is configured to apply a first force to said leaflets upon expansion thereby forming a continuous filter surface and continuous contact and/or a seal of said leaflets with surfaces of an aorta.

3. The device of claim 1, wherein said supporting elements are configured to apply a second force to said leaflets, said second force maintaining a continuous filter surface and contacting said leaflets with an adjacent leaflet, thereby forming a seal between said leaflets.

4. The device of claim 1, wherein said wire or said supporting elements comprise a metal, metal alloy, shape memory material, plastic, polymer, silicone, ceramic, or a composite thereof.

5. The device of claim 1, wherein said supporting elements comprise two or more loops, chains, wires, fibers, or combinations thereof or said expanding element comprises one or more loops, twisted loops, circular elements, semicircular elements, or ovular elements.

6. The device of claim 1, wherein said supporting elements comprise a rigid, semi-rigid, or flexible material; or said expanding element comprises a flexible or semi-rigid material.

7. The device of claim 1, wherein said expanding element is reversibly extended by (a) activation from said wire or a controllable catheter or (b) twisting said wire or a controllable catheter.

8. The device of claim 1, wherein said filter material comprises:
   (a) a pore size between about 50 microns (µm) to about 1000 µm (b) a plurality of woven fibers;
(c) a mesh or a nitinol mesh; or
(d) a flexible metal, a plastic, a polymer, a silicone, or a composite thereof.

9. The device of claim 1, the device comprising:
   (a) at least four, at least five, or at least six supporting elements;
   (b) at least two, at least three, at least four, at least five, or at least six expanding elements; or
   (c) at least three, at least four, at least five, or at least six leaflets.

10. The device of claim 1, wherein said device comprises a secondary frame comprising a wire having a proximal end and a distal end, said distal end attached to said second end of said primary frame and said proximal end attached to a controllable catheter, said wire of said secondary frame having at least one stabilizing element attached to said wire between said distal and proximal ends and configured to simultaneously contact both superior and inferior surfaces of the aorta.

11. The device of claim 10, wherein said stabilizing element is reversibly extended by (a) activation from said wire or the controllable catheter or (b) twisting said wire or a controllable catheter.

12. The device of claim 1, wherein said wire comprises a tube comprising an opening at the proximal end of said filter or an aspirating tube configured to remove particles from said proximal end of said filter by applying a vacuum.

13. A method of filtering particles in an aorta comprising deploying the device of claim 1 in an aorta.

14. A method of filtering particles in an aorta comprising:
   a. collapsing one or more elements of a device of anyone of claim 1,
   b. inserting said device into a catheter,
   c. inserting said catheter into an aortic arch,
   d. inserting said device into said aortic arch by removing said device from said catheter,
   e. expanding said one or more elements of said device,
   f. filtering blood flow,
   g. collapsing said one or more elements of said device,
   h. inserting said device into said catheter, and
   i. removing said catheter and said device.

15. The method of claim 14, wherein said device comprises an aspirating tube and a vacuum source, and said particles are removed during step f) and before step h) by aspiration of said device.

* * * * *